US006632397B1

(12) United States Patent
Henderson et al.

(10) Patent No.: US 6,632,397 B1
(45) Date of Patent: Oct. 14, 2003

(54) MULTI-PART ANTI-MICROBIAL CONCENTRATE SYSTEM, ACTIVATED SOLUTION, USE-DILUTION SOLUTION, METHOD OF MAKING SAME, AND METHOD OF STERILIZING WITH THE USE-DILUTION SOLUTION

(75) Inventors: Mary Beth Henderson, Minneapolis, MN (US); Patricia M. Stanley, Minneapolis, MN (US); Bradley K. Onstad, Champlin, MN (US)

(73) Assignee: Minntech Corporation, Minneapolis, MN (US)

(*) Notice: Subject to any disclaimer, the term of this patent is extended or adjusted under 35 U.S.C. 154(b) by 0 days.

(21) Appl. No.: 09/409,344

(22) Filed: Sep. 30, 1999

Related U.S. Application Data (60) Provisional application No. 60/102,663, filed on Oct. 1, 1998, and provisional application No. 60/102,664, filed on Oct. 1, 1998.

(51) Int. Cl.[7] .............................. A61L 9/00; B01J 19/00; B01D 11/04; B01D 11/02
(52) U.S. Cl. .............................. 422/28; 422/1; 422/32; 422/34; 422/40; 422/256; 422/261
(58) Field of Search ............................. 422/1, 28, 40, 422/256, 261, 292

(56) References Cited

U.S. PATENT DOCUMENTS

| | | | |
|---|---|---|---|
| 3,912,450 A | 10/1975 | Boucher | 21/54 A |
| 3,968,248 A | 7/1976 | Boucher | 424/333 |
| 4,731,222 A | 3/1988 | Kralovic | 422/37 |
| 4,885,253 A | 12/1989 | Kralovic | 435/296 |
| 4,892,706 A | 1/1990 | Kralovic | 422/28 |
| 4,917,815 A * | 4/1990 | Beilfuss et al. | |
| 5,037,623 A | 8/1991 | Schneider | 422/292 |
| 5,059,417 A | 10/1991 | Williams et al. | |
| 5,077,008 A | 12/1991 | Kralovic | 422/37 |
| 5,091,343 A | 2/1992 | Schneider | 422/297 |

(List continued on next page.)

FOREIGN PATENT DOCUMENTS

| | | |
|---|---|---|
| CA | 1 321 137 | 8/1993 |
| EP | 0 231 632 | 8/1987 |
| EP | 0 232 170 | 8/1987 |
| EP | 0 332 310 | 9/1989 |
| EP | 0 395 296 | 10/1990 |
| EP | 0 688 302 | 12/1995 |
| EP | 0 851 025 | 7/1998 |
| JP | 0 397 352 | 11/1990 |
| WO | WO 95/24388 | 9/1995 |
| WO | WO 95/32625 | 12/1995 |

OTHER PUBLICATIONS

BASF Performance Chemicals Pluronic & Tetronic Surfactants Brochure, 1996, pp. 1–37.

Almeida et al, "Improved Performance of Phosphoric Acid Anti–Corrosive Pretreatments when Aluminium Hydroxide is Added", 1995, pp. 6–11.

(List continued on next page.)

Primary Examiner—Robert J. Warden, Sr.
Assistant Examiner—Monzer R. Chorbaji
(74) Attorney, Agent, or Firm—Nixon & Vanderhye PC (57) ABSTRACT

The present invention relates to a two-part or multi-part concentrate system for preparing an activated solution which can be diluted with water to a use-dilution solution having improved anti-corrosive properties at room temperature. The concentrate system contains a first component containing at least one oxidizing agent, preferably hydrogen peroxide and a second component containing at least formic acid in a concentration of about 25 wt %. At least one corrosion inhibitor and at least one surfactant are also included in the concentrate system. When mixed and diluted, the resulting solution is excellent in its sterilization and anti-corrosive properties.

44 Claims, 6 Drawing Sheets

U.S. PATENT DOCUMENTS

| | | | |
|---|---|---|---|
| 5,116,575 A | 5/1992 | Badertscher | 422/28 |
| 5,122,365 A | 6/1992 | Murayama | |
| 5,122,538 A | 6/1992 | Lokkesmoe | 514/557 |
| 5,171,564 A | 12/1992 | Nathoo et al. | |
| 5,200,189 A | 4/1993 | Oakes et al. | |
| 5,208,013 A | 5/1993 | Klein | 424/59 |
| 5,209,909 A | 5/1993 | Siegel | 422/292 |
| 5,217,698 A | 6/1993 | Siegel | 422/295 |
| 5,236,135 A | 8/1993 | Wilson | 241/21 |
| 5,240,187 A | 8/1993 | Wilson | 241/21 |
| 5,314,687 A | 5/1994 | Oakes et al. | |
| 5,350,563 A | 9/1994 | Kralovic | 422/28 |
| 5,374,394 A | 12/1994 | Kralovic | 422/28 |
| 5,401,495 A | 3/1995 | Murayama | |
| 5,407,685 A | 4/1995 | Malchesky | 424/449 |
| 5,439,654 A | 8/1995 | Kochte | 422/292 |
| 5,508,046 A | 4/1996 | Cosentino | 424/616 |
| 5,518,927 A | 5/1996 | Malchesky | 436/1 |
| 5,534,221 A | 7/1996 | Hillebrenner | 422/33 |
| 5,552,115 A | 9/1996 | Malchesky | 422/28 |
| 5,589,507 A | 12/1996 | Hall, II | 514/557 |
| 5,616,335 A | 4/1997 | Nicolle | 424/405 |
| 5,616,616 A | 4/1997 | Hall, II | 514/557 |
| 5,620,656 A | 4/1997 | Wensky | 422/28 |
| 5,624,634 A | 4/1997 | Brougham | 422/28 |
| 5,635,195 A * | 6/1997 | Hall, II et al. | |
| 5,653,970 A | 8/1997 | Vermeer | 424/70.24 |
| 5,656,302 A | 8/1997 | Cosentino et al. | |
| 5,696,046 A | 12/1997 | Green | 502/161 |
| 5,718,910 A | 2/1998 | Oakes et al. | 424/405 |
| 5,720,983 A | 2/1998 | Malone | 424/616 |
| 5,736,057 A | 4/1998 | Minotti | 210/759 |
| 5,763,378 A | 6/1998 | Painter et al. | 510/224 |
| 5,858,117 A * | 1/1999 | Oakes et al. | |
| 5,861,366 A * | 1/1999 | Ihns et al. | |
| 5,900,256 A * | 5/1999 | Scoville, Jr. et al. | |

OTHER PUBLICATIONS

Agrawal et al, "Developments in Anti–Corrosive Pigments", Oct. 1995, pp. 49–53.

Boucher, "On Biocidal Mechanisms in the Aldehyde Series", 1975, pp. 1–7.

PMS Specialties Group, "Cobratec® Analytical Procedures Bulletin", 1990, pp. 1–10.

Block, "Disinfection, Sterilization, and Preservation", 1991, O'Connor et al, "Phenolic Compounds" Chapter 12, pp. 204, 216, 219; Merianos, "Quarternary Ammonium Antimicrobial Compounds", Chapter 13, pp. 225 and 248.

Russell et al, "Principles and Practice of Disinfection, Preservation and Sterilization", 1991, pp. 89, 98–101.

* cited by examiner

Fig. 3

Effect of Phosphoric Acid on Corrosion Reduction of Use-Dilution Sterilizing Solution at 45 Degrees

Fig. 5

The Structure of PLURONIC® Surfactants

Fig. 6

The Structure of PLURONIC® R Surfactants

Fig. 7

The Structure of TETRONIC® Surfactants

Fig. 8

The Structure of TETRONIC® R Surfactants

MULTI-PART ANTI-MICROBIAL CONCENTRATE SYSTEM, ACTIVATED SOLUTION, USE-DILUTION SOLUTION, METHOD OF MAKING SAME, AND METHOD OF STERILIZING WITH THE USE-DILUTION SOLUTION

This application claims the benefit of U.S. Provisional Application Ser. No. 60/102,663, which was filed Oct. 1, 1998, the disclosure of which is incorporated herein by this reference. This application also claims the benefit of U.S. Provisional Application Ser. No. 60/102,664, which was filed Oct. 1, 1998, the disclosure of which is incorporated herein by this reference.

BACKGROUND OF THE INVENTION

1. Field of the Invention

This invention relates to a sterilization solution, termed a use-dilution solution, capable of sterilizing at room temperature, a multi-part or two-part concentrate system suitable for preparing the use-dilution solution, a method for preparing the use-dilution solution, and a method of sterilizing with the use-dilution solution. This invention also relates to an anti-corrosive agent suitable for use in the microbicide of the present invention.

2. Description of Related Art

Conventionally, medical instruments have been sterilized or disinfected by introducing them into a high temperature/high pressure autoclave. Despite their effectiveness in killing microorganisms and the like, autoclaves are associated with several significant disadvantages. There are high capital and maintenance costs of autoclaves. Moreover, many medical instruments cannot withstand the high temperature and pressures associated with autoclave use. Another drawback is the cycle time of autoclaves, which may last for anywhere from several minutes to several hours.

As an alternative to autoclaves, ethylene oxide gas has been used in sealed sterilization chambers operated at elevated pressures. However, this conventional method is plagued by long cycle times, requiring long exposure times in a vacuum and even longer aeration times. Further, ethylene oxide gas is not effective in sterilizing all types of medical devices, and is highly toxic.

In order to circumvent some of the problems associated with autoclaves and ethylene oxide gas chambers, liquid sterilization solutions have been proposed. However, many conventional liquid sterilants require relatively long immersion times in order to assure sterilization as measured by elimination of bacterial endospore viability. For example, gluteraldehyde, a conventional sterilant which causes respiratory problems, takes 10 hours at room temperature for 100% kill of bacterial endospores. Moreover, many liquid sterilants are unacceptably corrosive, even those containing corrosion inhibitors, especially with respect to metal parts, particularly brass, copper, and aluminum.

SUMMARY OF THE INVENTION

It is therefore an object of this invention to overcome the above-mentioned problems by providing an anti-microbial, use-dilution sterilization solution that is capable of sterilizing objects containing bacterial spores, at room temperature, yet exhibits superior anti-corrosive properties.

In accordance with the principles of this invention, these and other objects are achieved by providing a multi-part concentrate system having a first component comprising hydrogen peroxide and water and a second component comprising formic acid and water. The first and second components are separate from each other. The system also includes a block copolymer of ethylene oxide and propylene oxide, phosphoric acid and benzotriazole, wherein each of the block copolymer, phosphoric acid and benzotriazole can be present in the first or second components. Typically, the first component contains 50 wt % hydrogen peroxide, 2.3 wt % C-99 with the remainder water; and the second component contains 25 wt % formic acid, 3.3 wt % L-44, 5.0 wt % phosphoric acid and the remainder water.

The first component and the second component are mixed together to form an initial activated sterilization solution which at time zero contains 30 wt % hydrogen peroxide, 10 wt % formic acid, 1.38 wt % C-99, 1.38 wt % L-44 and 2.0 wt % phosphoric acid.

When the initial activated sterilization solution reaches equilibrium, the resulting activated solution contains 25 wt % hydrogen peroxide, 6.5 wt % formic acid, 4.5–5.0 wt % performic acid, 1.38 wt % C-99, 1.38 wt % L-44, 2.0 wt % phosphoric acid and the remainder water. The resulting activated solution comprises about 30 wt % to about 40 wt % of an active anti-microbial composition and about 70 wt % to about 60 wt % water.

The resulting activated solution is further diluted with water to form a use-dilution solution that is used for sterilizing. The use-dilution solution comprises:

about 0.05 wt % to about 0.5 wt % performic acid, more preferably about 0.1 wt % to 0.5 wt % and most preferably 0.3 wt %;

about 0.4 wt % to about 6.0 wt % hydrogen peroxide, more preferably about 3.0 wt % to about 6.0 wt % and most preferably about 5.0 wt % to about 5.5 wt %;

preferably about 0.07 wt % to about 1.5 wt % formic acid, and most preferably about 0.05 wt % to 1.5 wt %;

preferably about 0.1 wt % to about 1.0 wt % benzotriazole, and most preferably 0.2 wt %;

preferably about 0.1 wt % to about 0.5 wt % and more preferably 0.2 wt % block copolymer of ethylene oxide and propylene oxide (also referred to herein as a polyoxypropylene-polyoxyethylene block copolymer); and preferably about 0.1 wt % to about 0.5 wt % phosphoric acid, and most preferably 0.3 wt %.

The anti-microbial composition use-dilution solution of the invention is useful as a sterilant. Sterilization means the absence of all detectable life forms, whether pathogenic or not. That is, sterilization means that a 100% kill of bacterial endospores is achieved. Sterilization is different than disinfection, which means the absence of pathogenic life forms. Thus, a sterilized instrument is also disinfected; however, the converse is not true: a disinfected instrument is not always sterilized.

Another object of this invention is to provide a two-part concentrate system or multi-part concentrate anti-microbial system, which is concentrated so as to facilitate storage, shelf-life and transfer, yet which can be diluted into a use-dilution sterilization solution which achieves a 100% kill of microorganisms including bacterial spores at room temperature.

In accordance with the principles of this invention, this and other objects can be achieved by the provision of a multi-part concentrate system which broadly includes: a first component comprising hydrogen peroxide and water; a second component comprising formic acid and water; also present as part of the multi-part concentrate system are a polyoxypropylene-polyoxyethylene block copolymer (also referred to herein as a block copolymer of ethylene oxide and propylene oxide); phosphoric acid; benzotriazole; and water. The block copolymer, phosphoric acid, and benzotriazole may be present in the first component and/or second component independently of one another or in a third component.

This invention also involves a method of making an activated intermediary solution from the above-described multi-part or two-part concentrate system. Specifically, when the two components of the two-part system are mixed together at appropriate ratios and diluted with water, an activated sterilization solution results that has reduced corrosive properties and can function as a sterilant upon further dilution to a use-dilution solution.

This invention further relates to a method of sterilizing a substrate, especially medical equipment, with the above-mentioned sterilization solution. In this regard, this method is especially suitable for sterilizing an object contaminated with bacterial spores, and may effectively be utilized at room temperature if desired. However, it is possible to use a temperature of from 45–55° C. to accelerate the active solution and to enhance efficacy of the use-dilution solution.

This invention still further relates to an anti-corrosive agent comprising phosphoric acid, block copolymer and benzotriazole. The anti-corrosive agent is suitable for use with anti-microbial compositions, especially compositions comprising performic acid, formic acid, and hydrogen peroxide.

These and other objects, features, and advantages of this invention will become apparent from the following detailed description when taken in conjunction with the accompanying drawings which illustrate, by way of example, the principles of this invention.

BRIEF DESCRIPTION OF THE DRAWINGS

The accompanying drawings facilitate an understanding of the various embodiments of this invention. In such drawings.

DESCRIPTION OF THE PREFERRED EMBODIMENTS

In accordance with one aspect of this invention, a multi-component concentrate system comprising at least two components or parts capable of being mixed and diluted with water into a sterilization solution exhibiting superior anti-corrosive properties is provided. In one embodiment, the first component comprises hydrogen peroxide and water, whereas the second component comprises formic acid and water.

The concentrate system further includes at least one surfactant, phosphoric acid, and at least one corrosion inhibitor. Preferably, the corrosion inhibitor(s) is/are contained in the first component and the surfactant(s) and phosphoric acid are contained in the second component.

Mixing of the first and second components causes the formic acid to react with the hydrogen peroxide to form performic acid. Preferably, the two-part or multi-part concentrate system is substantially free of any alcohol that is reactable with the formic acid to form an ester, e.g., ethyl formate, methyl formate, propyl formate to keep formic acid available for reaction. It is also preferred that the two-part or multi-part concentrate system be devoid of a sulfur-containing catalyst.

The surfactant incorporated into the two-component concentrate system should have a synergistic effect of making the resulting sterilization solution more efficacious and more rapid with respect to its germicidal effect. The surfactant used could be any of a class of zwitterionic, amphoteric, anionic, nonionic or cationic, and should be soluble in either of two concentrate components, preferably formic acid, and should be low foaming as to require fewer rinse cycles. Preferred for the purposes of this invention are PLURONIC (L-44), PLURONIC-R, TETRONIC, and TETRONIC-R surfactants, the chemical structures for these block copolymer surfactants are shown in FIGS. 5–8, respectively. These surfactants are available from BASF of Parsippany, NJ. These surfactants disrupt the microbes' surface membranes making them more porous and permeable and allowing the chemical microbicide to enter. The surfactant may be incorporated into the first component and/or the second component, or added separately as a third component; however it is preferable to incorporate the surfactant in the component containing formic acid to eliminate the formation of oxidative by-products produced by the hydrogen peroxide reacting with the surfactant upon storage and to insure a homogenous solution. Most preferably, the surfactant is PLURONIC L-44 block copolymer having an ethylene oxide block sandwiched between two propylene oxide blocks (see FIG. 5).

The surfactant incorporated into the two-component concentrate system should have a synergistic effect of making the resulting sterilization solution more efficacious and more rapid with respect to its germicidal effect. The surfactant used could be any of a class of zwitterionic, amphoteric, anionic, nonionic or cationic, and should be soluble in either of two concentrate components, preferably formic acid, and should be low foaming as to require fewer rinse cycles. Preferred for the purposes of this invention are PLURONIC (L-44), PLURONIC-R, TETRONIC, and TETRONIC-R surfactants, the chemical structures for these block copolymer surfactants are shown in FIGS. 5–8, respectively. These surfactants are available from BASF of Parsippany, N.J. These surfactants disrupt the microbes' surface membranes making them more porous and permeable and allowing the chemical microbicide to enter. The surfactant may be incorporated into the first component and/or the second component, or added separately as a third component; however it is preferable to incorporate the surfactant in the component containing formic acid to eliminate the formation of oxidative by-products produced by the hydrogen peroxide reacting with the surfactant upon storage and to insure a homogenous solution. Most preferably, the surfactant is PLURONIC L-44 block copolymer having an ethylene oxide block sandwiched between two propylene oxide blocks (see FIG. 5).

The corrosion inhibitor is preferably 1,2,3-benzotriazole (C-99), supplied by PMC Specialties Group, Inc. The corrosion inhibitor may also be incorporated into the first component and/or the second component, or added separately as a third component; however, it is preferable to incorporate the corrosion inhibitor in the component containing hydrogen peroxide because of enhanced chemical stability in a non-acidic environment.

In a preferred embodiment, the multi-part concentrate system is a two-component system, with the first component comprising about 30 wt % to about 50 wt % of hydrogen peroxide, and about 1.8 wt % to about 10 wt % of benzotriazole and the remainder water; and the second component comprising about 20 wt % to about 95 wt % of formic acid, about 2.5 wt % to about 12 wt % of block copolymer, and about 4 wt % to about 20 wt % of phosphoric acid and the remainder water.

More preferably, the two-component system comprises about 40 wt % to about 50 wt % of hydrogen peroxide, and about 1.8 wt % to about 2.3 wt % of benzotriazole and the remainder water; and the second component comprises about 20 wt % to about 30 wt % of formic acid, about 2.5 wt % to about 4 wt % of block copolymer, and about 4 wt % to about 6 wt % of phosphoric acid and the remainder water.

Still even more preferably, the first component comprises about 50 wt % of the hydrogen peroxide, about 2.3 wt % of benzotriazole, and the remainder water, while the second component comprises about 25 wt % of formic acid, about 3.3 wt % of block copolymer, and about 5.0 wt % of phosphoric acid, and the remainder water. In this embodiment, the ratio of the first component to the second component is preferably about 60:40.

The first and second components (and any additional components) of the concentrate system may be packaged physically separate from each other and mixed before use.

To form an activated solution, the first and second components are mixed together, preferably in a ratio of about 60:40. The resulting activated solution is preferably about 10 wt % formic acid, about 1.38 to 1.4 wt % block copolymer (L-44), about 0.1–2.0 wt % phosphoric acid, about 30 wt % $H_2O_2$, about 1.38 to 1.4 wt % benzotriazole (C-99) and the remainder water. More preferably, the initial activated solution contains 1.38 wt % C-99 and 1.38 wt % L-44. Within minutes at 45°–55° C. and within hours at room temperature, the activated solution reaches equilibrium wherein the composition contains: about 25 wt % hydrogen peroxide, about 6.5 wt % formic acid, about 4.5 to 5.0 wt % performic acid, 1.38 wt % C-99, 1.38 wt % L-44 and 2.0 wt % $H_2PO_4$, and the remainder water. The weight percentages of C-99, L-44 and $H_2PO_4$ do not change from time zero to equilibrium. The $H_2O_2$ to formic/performic acid ratio is preferably 1:0.33.

The two-part or multi-part concentrate system is mixed to form the activated solution and is allowed to react for approximately 0.5–30 minutes. The speed of reaction time in forming the activated solution is critically important for market acceptance of the product. The reaction time of the present invention is an advantageously short reaction time. The activated solution can preferably be mixed in a machine because of its low foaming quality but also can be mixed manually. The mixing and reaction time for component A and B is 30–60 minutes at room temperature and 5–10 minutes at 45–55° C. before the activated solution is ready for further dilution and use.

The activated solution may be used for as long as 48 hours after activation before the performic acid in the solution diminishes, affecting ultimate efficacy. Therefore, the components A and B are generally packaged and stored as two-separate packaging system components and are preferably mixed at a user's facility shortly before actual use.

If much less than about 25 wt % of formic acid is used in the concentrate system, the reaction to form the activated solution will not proceed quickly enough. It is important that the reaction proceed quickly in order to generate on demand the active anti-microbial component at effective concentrations.

To make a use-dilution solution, the activated solution is diluted to a ratio of from 2–17 wt % of activated solution to from 98–83 wt % of water. The use-dilution solution achieves a 100% kill of bacterial spores at 40°–50° C. in 15 minutes or less. The above ratio of hydrogen peroxide to formic/performic acid in the active solution is most effective in achieving a 100% kill of bacterial spores in 20 minutes or less.

The use-dilution solution comprises:

about 0.05 wt % to about 0.5 wt % performic acid, more preferably about 0.1 wt % to 0.5 wt % and most preferably 0.3 wt %;

about 0.4 wt % to about 6.0 wt % hydrogen peroxide, more preferably about 3.0 wt % to about 6.0 wt % and most preferably about 5.0 wt % to about 5.5 wt %;

about 0.07 wt % to about 1.5 wt % formic acid, and most preferably about 0.05 wt % to 1.5 wt %;

preferably about 0.1 wt % to about 1.0 wt % benzotriazole, and most preferably 0.2 wt %;

preferably about 0.1 wt % to about 0.5 wt % and more preferably 0.2 wt % block copolymer of ethylene oxide and propylene oxide (also referred to herein as a polyoxypropylene-polyoxyethylene block copolymer);

preferably about 0.1 wt % to about 0.5 wt % phosphoric acid, and most preferably 0.3 wt %;

and the remainder water.

Purified water is not required for diluting the activated solution to achieve the use-dilution solution. Commercially, this is a significant advantage, because tap water is more readily available and is less expensive to provide than purified or deionized water and more convenient for the end user.

The synergistic effect among the ethylene oxide/propylene oxide block-copolymer, the benzotriazole, and phosphoric acid (collectively referred to herein as the anti-corrosive system) surprisingly reduces corrosion by a factor of 10 over simply one or two of the elements alone. As mentioned above, the multi-part concentrate system is operative without the intervention of and is preferably substantially free of sulfur-containing catalysts, such as sulfuric and sulfonic acid catalysts, that interfere with the anti-corrosive properties exhibited by the synergism of the anti-corrosive system.

The two-part concentrate system, activated solution and use-dilution solution are all biodegradable. The concentrations selected for the activated solution are cost effective because they minimize the amount of aqueous solution needed, and reduce the time necessary to form the active ingredients (i.e. $H_2O_2$ and PFA) in the temperature range of 20–55° C. to become an effective sporicidal agent.

The two-part concentrate system can be stored for up to one year. After mixing the first and second components together, the activated solution must be further diluted to form the use-dilution solution. The use-dilution solution must be used within 48 hours because performic acid will degrade in the activated solution to a point where a use-dilution formulation will no longer be efficacious, i.e. kill spores within the desired amount of time.

To sterilize instruments, substrates, surfaces, etc., the use-dilution solution is applied to the object to be sterilized. Preferably, the use-dilution solution is applied within 1 hour of preparation at room temperature. Depending on the surface composition of the substrate (e.g. porous vs. non-porous, smooth vs. creviced) the use-dilution solution kills 100% of spores in 1–30 minutes at room temperature (20–25° C.). At elevated temperatures (40–50° C.) the use-dilution solution achieves 100% kill in 1–30 minutes and in as little as from 1–5 minutes, depending on the surface composition of the substrate. The period of time that the instruments are exposed to the use-dilution solution should be set to a period in which 100% of all microorganisms are killed. The composition of the invention is also useful at a temperature range of 20–50° C.

The instruments are then rinsed with sterile water until free of the sterilizing solution and are then sterile and ready for reuse or for storage in sterile packaging.

The composition of the invention is particularly useful for sterilizing medical instruments such as instruments with lumens, endoscopes, surgical instruments, dental instruments, dialiyzers, and most other medical devices and instrumentation that can be reused. The solution may be used on metal parts, particularly brass, copper, aluminum, and steel, as well as on plastic parts.

EXAMPLES

The principles of this invention will now be explained in further detail with reference to the following examples, which are not meant to limit or restrict the scope of this invention, but rather are provided to facilitate an understanding of the unexpected advantages associated with the use of the sterilization solution of this invention.

The following experiments were conducted to determine the corrosiveness of the sterilization solution compared to solutions having alternative anti-corrosive systems.

Example 1

1. Brass coupons were prepared, leaving aside one coupon that underwent all cleaning treatments but no corrosion treatments. This coupon is designated as the cleaning blank. Preparation was accomplished by placing the coupons in the rack of a cleaning tray with a clean forceps, while ensuring that no part of the brass came into contact with any foreign material.

2. The tray was dipped in an ultrasonic acetone bath and sonicated three times for at least 30 seconds. The coupons were allowed to air dry completely and then were weighed. (Weight 1)

3. For each of the solutions to be tested, one coupon was placed in one of the plastic specimen cups filled with the solution to be tested. The solutions are as follows:

A=Use-dilution solution in accordance with the present invention (UDS)
B=UDS+0.2% Cobratec-99
C=UDS+0.3% $H_3PO_4$
D=UDS+0.2% Pluronic L-44
E=UDS+0.3% $H_3PO_4$+0.2% Cobratec-99
F=UDS+0.3% $H_3PO_4$+0.2% Pluronic L-44
G=UDS+0.2% Cobratec-99+0.2% Pluronic L-44
H=UDS+0.3% $H_3PO_4$+0.2% Pluronic L-44+0.2% Cobratec-99.

4. The coupons were allowed to soak for 3–5 hours at room temperature.

5. After the soaking period, the coupons were placed in the rack, and the rack was placed in a cleaning tray of the ultrasonic cleaner. The tray was filled with enough 10% $H_2SO_4$ to cover the coupon completely and was sonicated for two minutes.

6. The coupons were removed from the tray and rinsed thoroughly with distilled water. The coupons were then removed with forceps from the tray and air dried with an air gun and/or left to air dry overnight.

7. The coupons were then weighed again (Weight 2).

8. The coupons were placed, one at a time on the back of the modified test tube rack, in-between the two glass slides. A Scotch Brite pad (product of 3M Corp.) was wrapped around a 1 Kg. mass and rubbed against the coupon 10 times each way, allowing the weight of the mass to be the only downward force exerted on the coupons. This procedure was applied to both sides of the coupons. The coupons were then weighed again. (Weight 3).

9. Visual changes and weight loss were evaluated.

10. The weight loss for each coupon in mg/min. was calculated.

Figure 1:
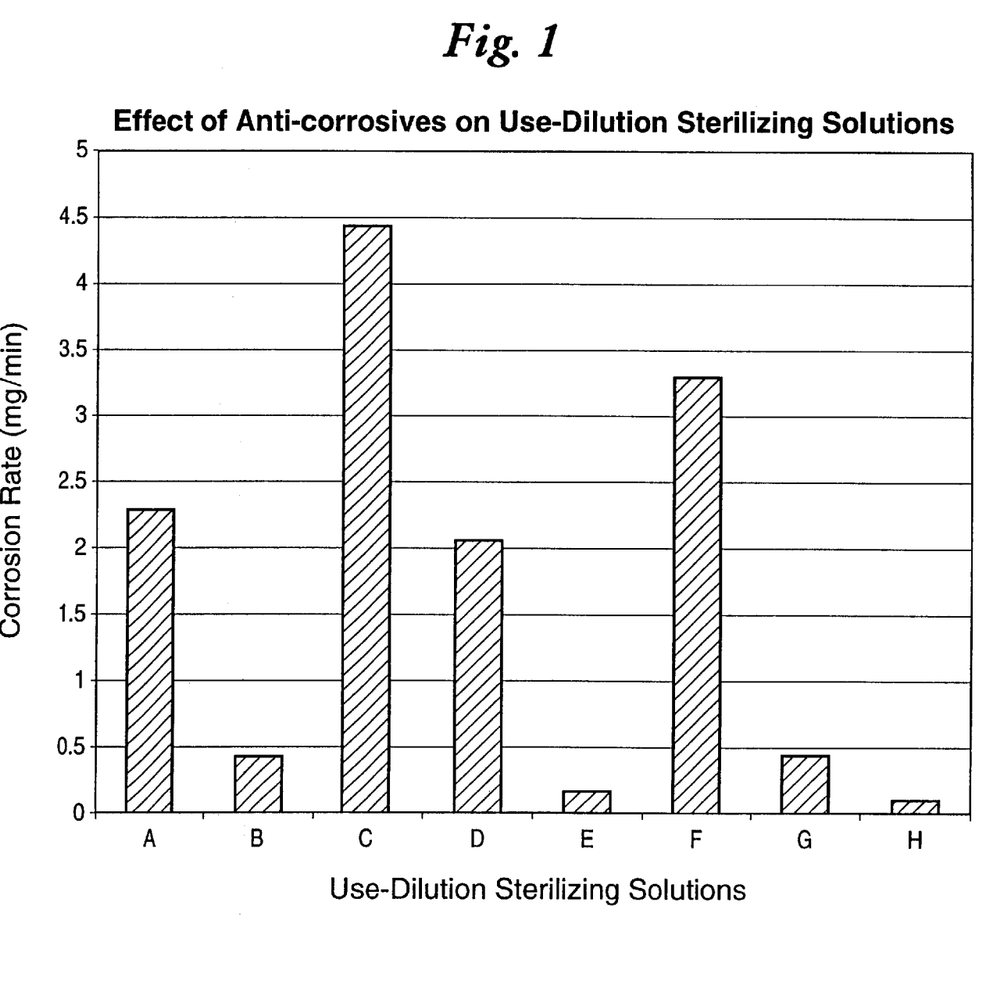
FIG. 1 is a graphical representation of the corrosion rate for various use-dilution sterilizing solutions in accordance with the present invention.

Referring now more particularly to the drawings, FIG. 1 is a graphical representation of the corrosion caused by different use-dilution sterilizing solutions, referred to hereinafter as UDS. In FIG. 1, UDS was tested alone to determine the corrosive effect on brass coupons. This was compared to UDS in combination with several anti-corrosive systems to determine the affect that the anti-corrosive systems have on the corrosiveness of UDS. In FIG. 1, UDS= 1.0% Formic Acid+4.0% $H_2O_2$+0.4% Performic Acid.

As shown in FIG. 1, when UDS was used alone (sample A), the corrosion rate was about 2.25 mg/min. On the other hand, when the inventive anti-corrosive system 0.3%$H_3PO_4$, 0.2% PLURONIC L-44, and 0.2% COBRATEC-99 was used with the UDS (sample H), the corrosion rate was significantly reduced to less than about 0.15 mg/min.

The synergistic effect realized by using the inventive anti-corrosive system is evident from a comparison of sample H with samples A–G.

Samples C and F each exhibited a greater corrosion rate (about 4.4 mg/min and about 3.3 mg/min, respectively) than the UDS alone (Sample A), thus signifying that the inclusion of phosphoric acid $H_3PO_4$ would be expected to increase the overall corrosiveness of the solution.

Despite the corrosive effect of the phosphoric acid, the inventive sample H exhibited a lower overall corrosiveness (about 0.15 mg/min) than samples B (0.4 mg/min), D (2.1 mg/min), and G (0.4 mg/min), which were devoid of phosphoric acid.

Thus, the inventors have concluded that the combination of the benzotriazole, block-copolymer surfactant, and phosphoric acid exhibits synergistic effects in the reduction of corrosion of brass coupons. The combination of the benzotriazole, block-copolymer surfactant, and phosphoric acid operates as an anticorrosive agent.

A separate anticorrosive agent can be packaged for addition to hydrogen peroxide and formic acid so that the resulting concentrations are as described above for the initial activated solution. The preferred ranges for the anti-corrosive agent prior to dilution to an activated solution or a use-dilution solution are 1.67 to 8.33 wt % phosphoric acid, 1.67 to 8.35 wt % block copolymer and 1.12 wt % to 11.15 wt % benzotriazole. The preferred range of the anticorrosive agent before dilution is 5.0 wt % phosphoric acid, 3.34 wt % block copolymer and 2.23 wt % benzotriazole.

Example 2

Figure 2:
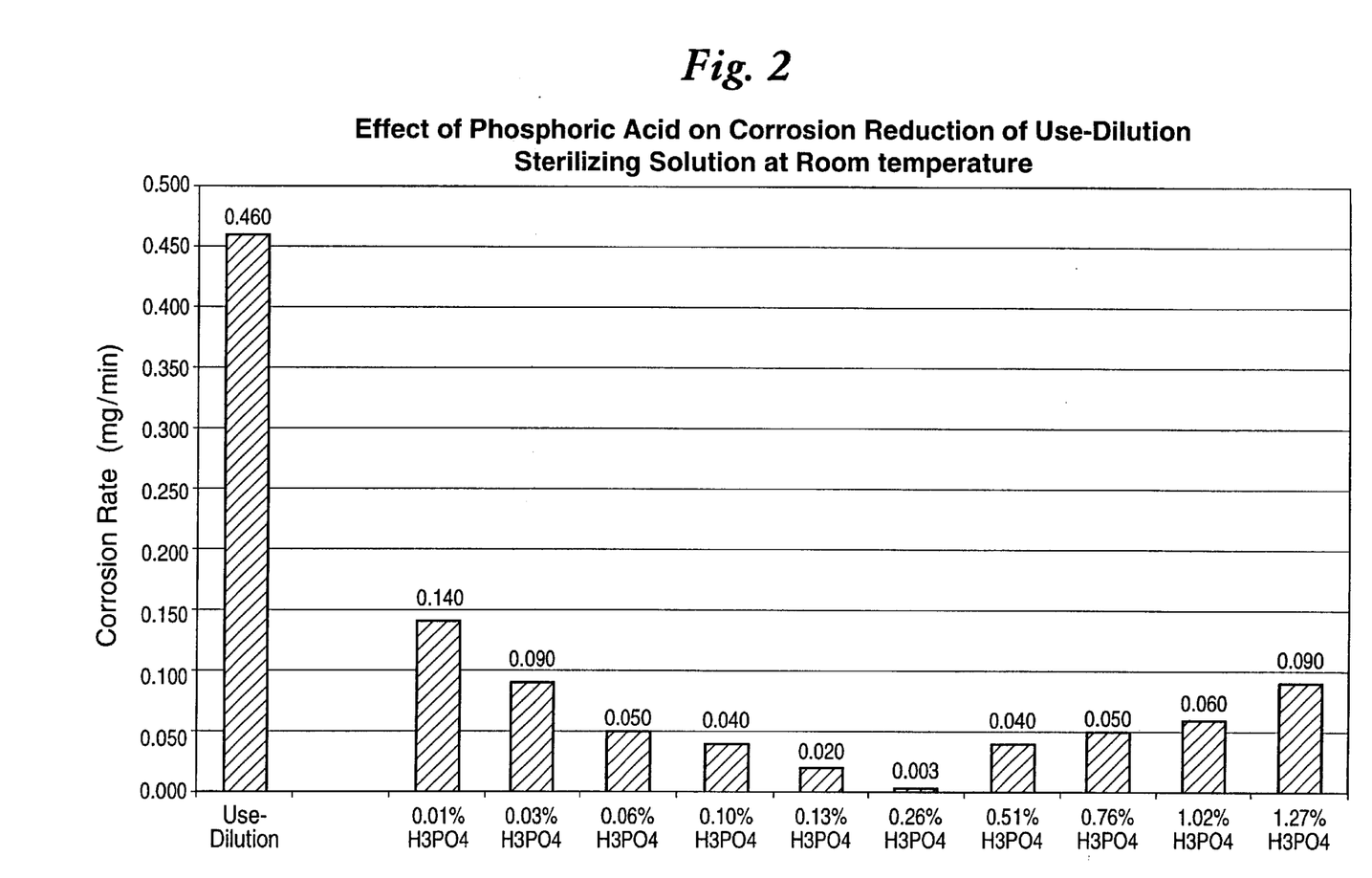
FIG. 2 is a graphical representation of a corrosion study of the use-dilution sterilizing solution in accordance with the present invention conducted by varying the phosphoric acid concentrations.

FIG. 2 is a graphical representation of a corrosion study of the UDS according to the invention alone and with different concentrations of phosphoric acid added. All formulations were tested using brass coupons and 300 minute exposure time to the testing solution. Parts A (50% $H_2O_2$ and 2.34% C-99) and B (25% formic acid and 3.34% L-44) of the two-part concentrate system were mixed for 1 hour at room temperature, $H_3PO_4$ was added to the concentrate and the concentrate was diluted 15/85 with water to form the use-dilution sterilizing solution.

It can be seen from the results presented in FIG. 2 that UDS alone exhibited a corrosion of 0.460 mg/min. UDS with 0.01% $H_3PO_4$ exhibited a corrosion rate of 0.140 mg/min, that the corrosion rate initially decreased as the phosphoric acid concentration was increased until it reaching 0.003 mg/min for UDS with 0.26% $H_3PO_4$, then steadily increased with increasing phosphoric acid concentration. (Brass corrosion of <0.1–0.2 mg/min. is an acceptable range with 0.13–0.4 wt % phosphoric acid)

Example 3

Figure 3:
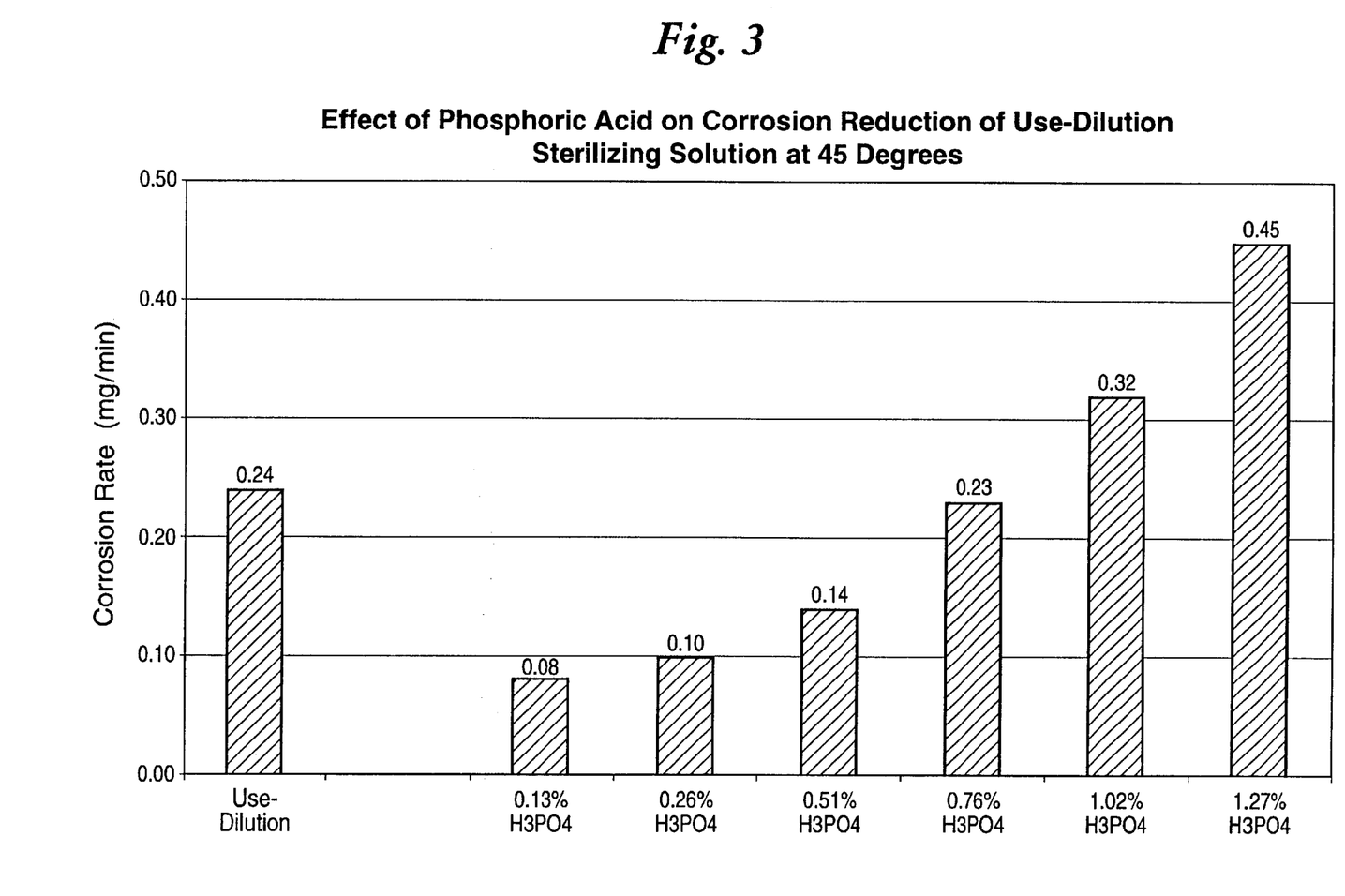
FIG. 3 is a graphical representation of a corrosion study of the use-dilution sterilizing solution in accordance with the present invention conducted by varying the phosphoric acid concentrations at 45° C.

FIG. 3 is a graphical representation of a corrosion study of UDS using different concentrations of phosphoric acid at 45° C. All the formulations were tested using brass coupons wherein each coupon was cycled, meaning each coupon was exposed to 10 batches of freshly made solution for 10 minutes each. Parts A (50% $H_2O_2$ and 2.34% C-99) and B (25% formic acid and 3.34% L-44) of the two-part concentrate system were mixed at 45° C. $H_3PO_4$ was added and RO (reverse osmosis) water at 45° C. was added to form the use-dilution. Brass coupons were exposed for 10 minutes at 45° C. The cycle was repeated 10 times.

As can be see from the results in FIG. 3, 0.13% to 0.76% $H_3PO_4$ addition lowered the corrosion rate as compared with UDS alone. However, the 1.02% and 1.27% $H_3PO_4$ addition increased the corrosion rate as compared to UDS alone.

Example 4

Figure 4:
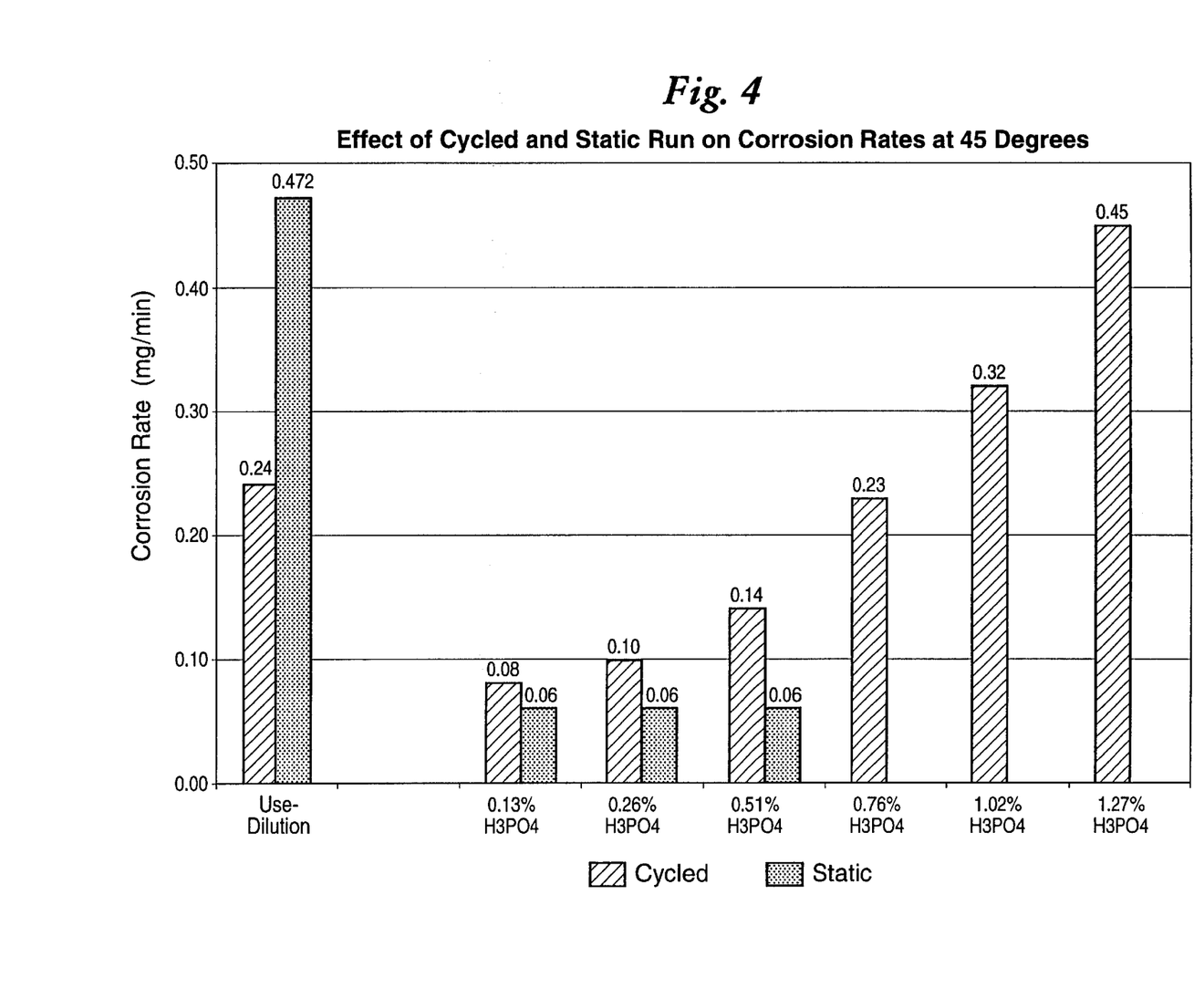
FIG. 4 is a graphical representation of a corrosion study of the use-dilution sterilizing solution in accordance with the present invention conducted by varying the phosphoric acid concentrations at 45° C. and comparing cycled and static runs.
Figure 5:
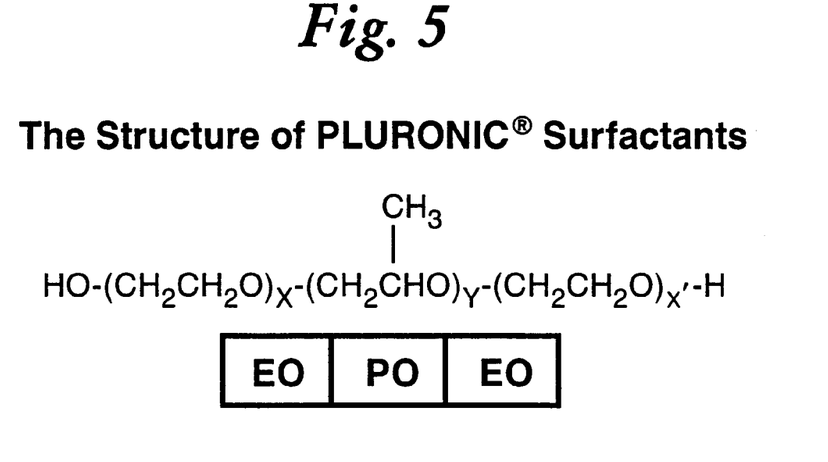
FIGS. 5–8 show the chemical structures of PLURONIC (L-44), PLURONIC-R, TETRONIC, and TETRONIC-R surfactants, respectively.
Figure 6:
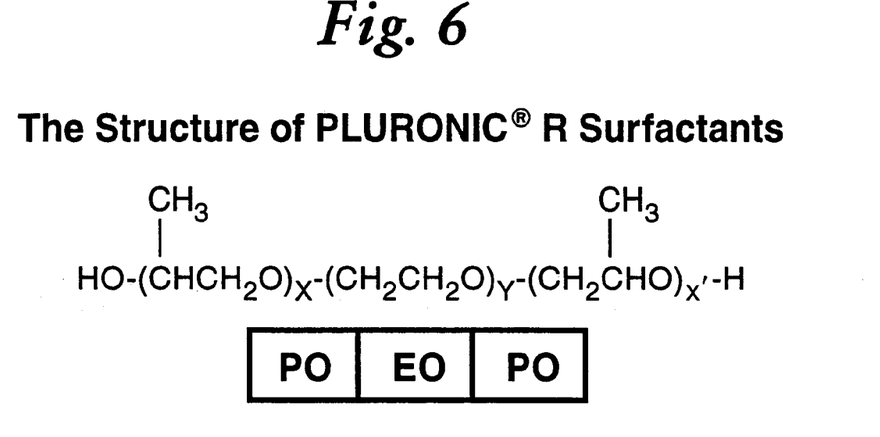
Figure 7:
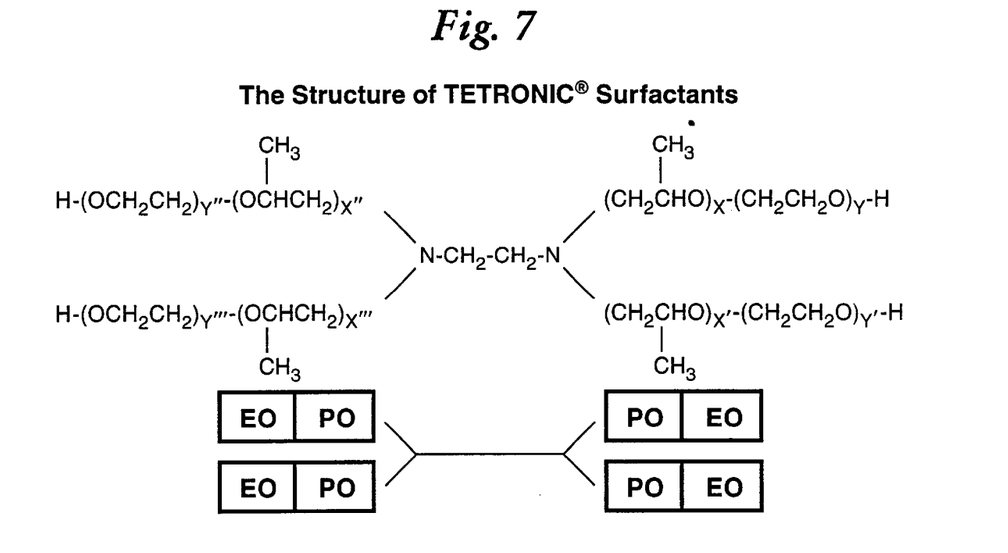
Figure 8:
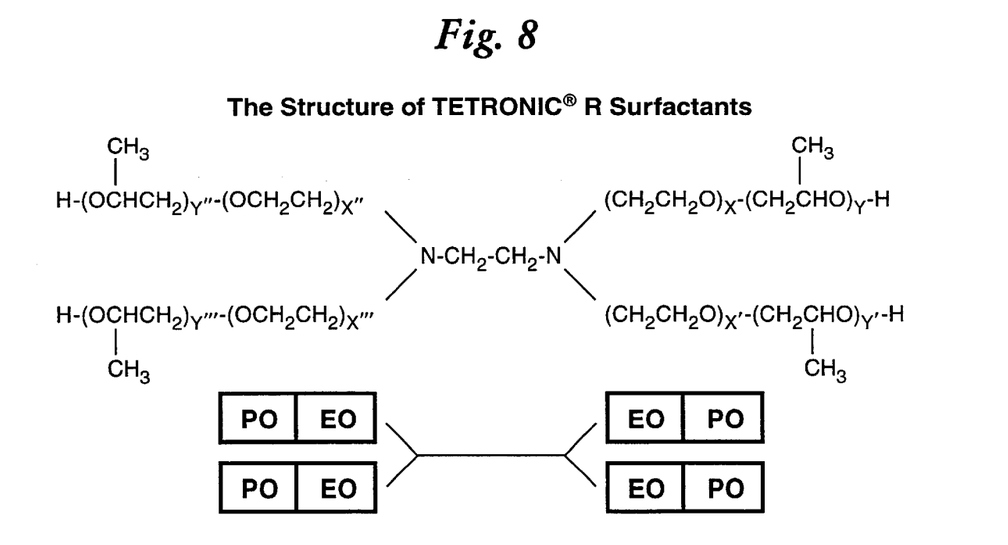

FIG. 4 is a graphical representation of a corrosion study of UDS using different concentrations of phosphoric acid at 45° C. and comparing cycled and static runs. The results in FIG. 4 also show that certain concentrations of $H_3PO_4$ decrease the corrosion rate of UDS and certain concentrations of $H_3PO_4$ increase the rate of corrosion of $H_3PO_4$.

Example 5

Table 1A and 1B are directed to a 10 minute sterilization at low levels of active ingredients (PFA and $H_2O_2$) for a variety of use-dilution solutions at room temperature (RT) and 50° C. on a variety of substrates, stainless steel, Teflon®, polyethylene component parts of medical devices.

100% kill=

[ ▫ ]

Spores remaining=

[ ▨ ]

The Tables 1A and 1B support that the multi-part concentration system can be made in a variety of ways. Note that the concentration for Part A and Part B in Tables 1A and 1B are different than the concentrations for Part A and Part B described above.

TABLE 1A

SPORICIDAL ACTIVITY OF NSX SOLUTIONS
WITH *BACILLU STEAROTHERMOPHILUS* SPORES ON VARIOUS SUBSTRATES

| Shelf life of Sol. A | Exp. Time min. | SS Room Temp. | | | SS 50 C. | | | Teflon Room Temp. | | | Teflon 50 C. | | |
|---|---|---|---|---|---|---|---|---|---|---|---|---|---|
| | | 15/85 | 5/95 | 2/98 | 15/85 | 5/95 | 2/98 | 15/85 | 5/95 | 2/98 | 15/85 | 5/95 | 2/98 |
| 0 day | 1 | — | | | — | — | | — | | | — | — | |
| | 3 | — | — | | — | — | — | — | — | | — | — | — |
| | 5 | — | — | | — | — | — | — | — | | — | — | — |
| | 10 | — | — | — | — | — | — | — | — | — | — | — | — |
| | 20 | — | — | — | — | — | — | — | — | — | — | — | — |
| | 30 | — | — | — | — | — | — | — | — | — | — | — | — |
| 1 day | 1 | — | | | — | | | — | | | — | | |
| | 3 | — | — | | — | — | | — | — | | — | — | |
| | 5 | — | — | | — | — | | — | — | | — | — | |
| | 10 | — | — | — | — | — | — | — | — | — | — | — | — |
| | 20 | — | — | — | — | — | — | — | — | — | — | — | — |
| | 30 | — | — | — | — | — | — | — | — | — | — | — | — |
| 2 days | 1 | — | | | — | — | | | | | | | |
| | 3 | — | — | | — | — | — | | | | | | |
| | 5 | — | — | | — | — | — | | | | | | |
| | 10 | — | — | — | — | — | — | | | | | | |
| | 20 | — | — | — | — | — | — | | | | | | |
| | 30 | — | — | — | — | — | — | | | | | | |
| 4 days | 1 | | | | — | — | | | | | | | |
| | 3 | | | | — | — | — | | | | | | |
| | 5 | — | — | | — | — | — | | | | | | |
| | 10 | — | — | | — | — | — | | | | | | |
| | 20 | — | — | — | — | — | — | | | | | | |
| | 30 | — | — | — | — | — | — | | | | | | |
| 7 days | 1 | | | | — | | | | | | | | |
| | 3 | — | — | | — | — | | | | | | | |
| | 5 | — | — | | — | — | | | | | | | |

TABLE 1A-continued

SPORICIDAL ACTIVITY OF NSX SOLUTIONS WITH *BACILLU STEAROTHERMOPHILUS* SPORES ON VARIOUS SUBSTRATES

|  |  |  |  |  |  |  |  |
|---|---|---|---|---|---|---|---|
|  | 10 | — | — | — | — | — |  |
|  | 20 | — | — | — | — | — |  |
|  | 30 | — | — | — | — | — |  |
| 14 days | 1 |  |  | — |  |  |  |
|  | 3 |  |  | — |  |  |  |
|  | 5 | — |  | — |  |  |  |
|  | 10 | — |  | — | — |  |  |
|  | 20 | — | — | — |  |  |  |
|  | 30 | — | — | — | — |  |  |

| Shelf life of Sol. A | Exp. Time min. | PU Room Temp. | | | PU 50 C. | | | PE Room Temp. | | | PE 50 C. | | |
|---|---|---|---|---|---|---|---|---|---|---|---|---|---|
|  |  | 15/85 | 5/95 | 2/98 | 15/85 | 5/95 | 2/98 | 15/85 | 5/95 | 2/98 | 15/85 | 5/85 | 2/98 |
| 0 day | 1 | — |  |  | — | — |  | — |  |  | — | — |  |
|  | 3 | — | — |  | — | — | — | — | — |  | — | — | — |
|  | 5 | — | — |  | — | — | — | — | — | — | — | — | — |
|  | 10 | — | — | — | — | — | — | — | — | — | — | — | — |
|  | 20 | — | — | — | — | — | — | — | — | — | — | — | — |
|  | 30 | — | — | — | — | — | — | — | — | — | — | — | — |
| 1 day | 1 | — | — |  | — | — |  | — | — |  | — | — |  |
|  | 3 | — | — |  | — | — | — | — | — |  | — | — | — |
|  | 5 | — | — |  | — | — | — | — | — | — | — | — | — |
|  | 10 | — | — | — | — | — | — | — | — | — | — | — | — |
|  | 20 | — | — | — | — | — | — | — | — | — | — | — | — |
|  | 30 | — | — | — | — | — | — | — | — | — | — | — | — |

|  | 0 day | 1 day | 2 days | 4 days | 7 days | 14 days |
|---|---|---|---|---|---|---|
| Positive control |  |  |  |  |  |  |
| SS | + | + | + | + | + | + |
| Teflon | + | + |  |  |  |  |
| PU | + | + |  |  |  |  |
| PE | + | + |  |  |  |  |
| Negative Control | – | – | – | – | – | – |

Solution A: active ingredients = 116.28 g of 51.5% peroxide + 21.04 g of formic acid + 62.68 g of water
Solution B: inert ingredients = 2.25 g of Cobratec-99 + 3.53 g of Pluronic F-68 1 L of water
15/85 = 15 parts of solution A + 85 parts of solution B (pH of 15/85 solution = 2.19)
5/95 = 5 parts of solution A + 95 parts of solution B (pH of 5/95 solution = 2.48)
2/98 = 2 parts of solution A + 98 parts of solution B (pH of 2/98 solution = 2.70)
Total SS samples = 216 + controls
Total Teflon samples = 72 + controls
Total PU samples = 72 + controls
Total PE samples = 72 + controls
The titer of *Bacillus stearothermophilus* spores per carrier = $1.7 \times 10^6$
Total amount of solution A needed = 600 g (prepare on 11/17 and store at room temperature for all tests)
(304 g of 59% peroxide + 63 g of formic acid + 233 g of water)
Total amount of solution B needed = 8 L (prepare on 11/17 and store at room temperature for all tests)
(2 × (9 g of cobratec-99 + 14.12 g of pluronic F-68 in 4 liter of water))
Each day needs 400 ml of 15/85 solution (200 ml for room temperature and 200 ml for 50° C.)
Each day needs 400 ml of 5/95 solution (200 ml for room temperature and 200 ml for 50° C.)
Each day needs 400 ml of 2/98 solution (200 ml for room temperature and 200 ml for 50° C.)
Total TSB tubes needed = 432 (1 drop of catalase + 10 drops of 0.2 N NaOH in the TSB tube)
TSB: lot # C8CPHC, Exp. Date 12/1/98

TABLE 1B

SPORICIDAL ACTIVITY OF NSX SOLUTIONS WITH *BACILLU STEAROTHERMOPHILUS* SPORES ON SS BLADES

| Shelf life of Solution | Exp. Time (min) | Aged solution A + Aged solution B | | | | | | Ages (solution A + solution B) | | | | | |
|---|---|---|---|---|---|---|---|---|---|---|---|---|---|
|  |  | Room Temperature | | | 50 C. | | | Room Temperature | | | 50 C. | | |
|  |  | 15/85 | 5/95 | 2/98 | 15/85 | 5/95 | 2/98 | 15/85 | 5/95 | 2/98 | 15/85 | 5/95 | 2/98 |
| 0 day | 1 | — |  |  | — |  |  | — |  |  | — |  |  |
|  | 3 | — | — |  | — | — |  | — | — |  | — | — |  |
|  | 5 | — | — |  | — | — | — | — | — |  | — | — | — |
|  | 10 | — | — | — | — | — | — | — | — | — | — | — | — |
|  | 20 | — | — | — | — | — | — | — | — | — | — | — | — |
|  | 30 | — | — | — | — | — | — | — | — | — | — | — | — |

TABLE 1B-continued

SPORICIDAL ACTIVITY OF NSX SOLUTIONS
WITH *BACILLU STEAROTHERMOPHILUS* SPORES ON SS BLADES

| Shelf life of Solution | Exp. Time (min) | Aged solution A + Aged solution B | | | | | | Ages (solution A + solution B) | | | | | |
|---|---|---|---|---|---|---|---|---|---|---|---|---|---|
| | | Room Temperature | | | 50 C. | | | Room Temperature | | | 50 C. | | |
| | | 15/85 | 5/95 | 2/98 | 15/85 | 5/95 | 2/98 | 15/85 | 5/95 | 2/98 | 15/85 | 5/95 | 2/98 |
| 1 day | 1 | — | | | — | — | | | | | — | | |
| | 3 | — | — | | — | — | — | | | | — | — | |
| | 5 | — | — | | — | — | — | — | | | — | — | |
| | 10 | — | — | — | — | — | — | — | | | — | — | — |
| | 20 | — | — | — | — | — | — | — | | | — | — | — |
| | 30 | — | — | — | — | — | — | — | | | — | — | — |

Solution A: active ingredients = 116.28 g of 51.5% peroxide + 21.04 g of formic acid + 62.68 g of water
Solution B: inert ingredients = 2.25 g of Cobratec-99 + 3.53 g of Pluronic F-68 1 L of water
15/85 = 15 parts of solution A + 85 parts of solution B
5/95 = 5 parts of solution A + 95 parts of solution B
2/98 = 2 parts of solution A + 98 parts of solution B Example 6

Sterilization solutions were tested on small circles of suture silk according to the standards of the U.S. Association of Official Analytical Chemists, Sporicidal Test. Suture silk is difficult to sterilize because of its fibrous and porous nature. To generate a sterilizing solution, Part A comprising 50 wt % of hydrogen peroxide and 2.34 wt % of C-99 was mixed with Part B comprising 25 wt % formic acid. The ratio of Part A to Part B was 60:40. After reaction at room temperature for 1 hour, the active solution was diluted with 85 wt % hard water containing various levels of surfactant (Pluronic L-44). Carriers inoculated with bacterial spores were exposed to the sterilizing solutions for 9 minutes at 35° C. The sterility of the carriers was determined with the following results:

| Surfactant Concentration (%) | Percent sterile carriers | |
|---|---|---|
| | Trial 1 | Trial 2 |
| 0 | 37% | 57% |
| 0.05 | 70% | ND* |
| 0.10 | 93% | ND |
| 0.15 | ND | 100 |
| 0.3 | ND | 100 |

*Not determined

The data show the importance of the surfactant in improving the efficacy of the product so that it is an efficient sterilant in a minimum exposure time.

The above test was repeated except that Part B also contained 5 wt % phosphoric acid and the exposure conditions were 7 minutes at 40° C.

| Surfactant Concentration (%) | Percent sterile carriers |
|---|---|
| 0 | 80 |
| 0.2 | 100 |

From the above, it can be seen that the surfactant was necessary for efficient sterilization.

The foregoing detailed description of the preferred embodiments of the invention has been provided for the purposes of illustration and description. It is not intended to be exhaustive or to limit the invention to the precise embodiments disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An anti-microbial concentrate system comprising:
    a first component comprising hydrogen peroxide and water;
    a second component comprising formic acid and water;
    a block copolymer of ethylene oxide and propylene oxide, said block copolymer being present in said first component, said second component, or said first and second components;
    phosphoric acid present in said first component, said second component, or said first and second components; and
    benzotriazole present in said first component, said second component, or said first and second components,
    wherein said first and second components are separated from each other.

2. The concentrate system of claim 1, wherein said second component contains said block copolymer and said phosphoric and, and further wherein said first component contains said benzotriazole.

3. The concentrate system of claim 2, wherein:
    said first component comprises about 30 wt % to about 50 wt % of said hydrogen peroxide, and about 2 wt % to about 10 wt % of said benzotriazole and the remainder water; and
    said second component comprises about 25 wt % to about 95 wt % of said formic acid, about 3 wt % to about 12 wt % of said block copolymer, and about 4 wt % to about 20 wt % of said phosphoric acid and the remainder water.

4. The concentrate system of claim 3, wherein:
    said first component comprises about 50 wt % of said hydrogen peroxide, about 2.3 wt % of said benzotriazole, and the remainder water; and said second component comprises about 25 wt % of said formic acid, about 3.3 wt % of said block copolymer, and about 5 wt % of said phosphoric acid, and the remainder water.

5. The concentrate system of claim 1, wherein said concentrate system is substantially free of an alcohol reactable with said formic acid to form an ester.

6. The concentrate system according to claim 1, wherein said concentrate system is devoid of a sulfur-containing catalyst.

7. The concentrate system of claim 1, wherein a ratio of said first component to said second component is 60:40.

8. The concentrate system of claim 1, wherein said benzotriazole is 1,2,3-benzotriazole and said block copolymer has an ethylene oxide block sandwiched between two propylene oxide blocks.

9. A use-dilution anti-microbial solution comprising:
   about 0.05 wt % to about 0.5 wt % performic acid;
   about 0.07 wt % to about 1.5 wt % formic acid;
   about 0.4 wt % to about 6.0 wt % hydrogen peroxide;
   about 0.1 wt % to about 0.5 wt % block copolymer of ethylene oxide and propylene oxide;
   about 0.1 wt % to about 0.5 wt % phosphoric acid;
   about 0.1 wt % to about 1.0 wt % benzotriazole; and
   a remainder water.

10. The use-dilution solution of claim 9, wherein said use-dilution solution comprises about 0.3 wt % performic acid, 0.05–1.5 wt % of said formic acid, about 5–5.5 wt % of said hydrogen peroxide, about 0.2 wt % of said block copolymer, about 0.3 wt % of said phosphoric acid, about 0.2 wt % of said benzotriazole, and the remainder water.

11. The use-dilution solution of claim 9, wherein said benzotriazole is 1,2,3-benzotriazole and said block copolymer has an ethylene oxide block sandwiched between two propylene oxide blocks.

12. A method of sterilizing an object comprising subjecting the object to the use-dilution solution of claim 9 to sterilize the object.

13. The method of claim 12, wherein said subjecting is performed at room temperature.

14. The method of claim 13, wherein said subjecting is performed from 1–30 minutes at said room temperature.

15. The method of claim 12, wherein said subjecting is performed at 40–50° C.

16. The method of claim 15, wherein said subjecting is performed from 1–30 minutes at 50° C.

17. The method of claim 12, wherein said subjecting is performed from about 1–30 minutes at from about 20° C. to about 50° C. to achieve sterilization.

18. A method of sterilizing an object comprising subjecting the object to the use-dilution solution of claim 10 to sterilize the object.

19. The method of claim 18, wherein said subjecting is performed at room temperature.

20. The method of claim 18, wherein said subjecting is performed at from 40° C. to 50° C.

21. The method of claim 20, wherein said subjecting is performed from 1–30 minutes at 50° C.

22. The method of claim 18, wherein said subjecting is performed from about 1–30 minutes at from about 20° C. to about 50° C. to achieve sterilization.

23. A method of sterilizing an object contaminated with bacterial spores comprising subjecting the object to the use-dilution solution of claim 9 to sterilize the object.

24. The method of claim 23, wherein said subjecting is performed at room temperature.

25. The method of claim 23, wherein said subjecting is performed at from 40° C. to 50° C.

26. The method of claim 25, wherein said subjecting is performed from 1–30 minutes at 50° C.

27. The method of claim 23, wherein said subjecting is performed from about 1–30 minutes at from about 20° C. to about 50° C.

28. A method of sterilizing an object contaminated with bacterial spores comprising subjecting the object to the use-dilution solution of claim 10 to sterilize the object.

29. The method of claim 28, wherein said subjecting is performed at room temperature.

30. The method of claim 28, wherein said subjecting is performed at from 40° C. to 50° C.

31. The method of claim 30, wherein said subjecting is performed from 1–30 minutes at 50° C.

32. The method of claim 28, wherein said subjecting is performed from about 1–30 minutes at from about 20° C. to about 50° C. to achieve sterilization.

33. A method of preparing a use-dilution solution comprising:
   (a) preparing a first component comprising about 30 wt % to about 50 wt % hydrogen peroxide, about 1.8 wt % to about 10 wt % benzotriazole and the remainder water;
   (b) preparing a second component comprising about 20 wt % to about 95 wt % formic acid, about 2.5 wt % to about 12 wt % block copolymer of ethylene oxide and propylene oxide, about 4 wt % to about 20 wt % phosphoric acid and the remainder water; and
   (c) mixing the first component and the second component in a weight ratio of 60:40 to form an activated solution; and
   (d) diluting the activated solution with water.

34. The method of claim 33, wherein said diluting involves mixing the activated solution and water in a weight ratio of 15:85.

35. The method of claim 33, wherein said diluting involves mixing the activated solution and water in a weight ratio of 5:95.

36. The method of claim 33, wherein said diluting involves mixing the activated solution and water in a weight ratio of 2:98.

37. The method of claim 33, wherein:
   the first component comprises about 50 wt % of the hydrogen peroxide, about 2.3 wt % of the benzotriazole and the remainder water; and
   the second component comprises about 25 wt % of the formic acid, about 3.3 wt % of the block copolymer, and about 5.0 wt % of the phosphoric acid, and the remainder water.

38. An anti-microbial activated solution at equilibrium comprising:
   25 wt % hydrogen peroxide;
   6.5 wt % formic acid;
   4.5 wt % to 5.0 wt % performic acid;
   1.38 wt % benzotriazole;
   1.38 wt % block copolymer of ethylene oxide and propylene oxide;
   2.0 wt % phosphoric acid; and
   a remainder of water to 100%.

39. The anti-microbial activated solution of claim 38, wherein said benzotriazole is 1,2,3-benzotriazole and said block copolymer has an ethylene oxide block sandwiched between two propylene oxide blocks.

40. An anti-corrosive system suitable for use with formic acid and hydrogen peroxide, said system comprising:

(a) phosphoric acid;

(b) benzotriazole; and (c) a block co-polymer of ethylene oxide and propylene oxide.

41. The anti-corrosive agent of claim 40, wherein said phosphoric acid is present in an amount from about 1.67 wt % to about 8.33 wt %, said benzotriazole is present in an amount from about 1.12 wt % to about 11.15 wt % and said block copolymer is present in an amount from about 1.67 wt % to about 8.25 wt %.

42. The anti-corrosive agent of claim 41, wherein said phosphoric acid is present in an amount of about 5.0 wt %, said benzotriazole is present in an amount of about 2.23 wt % and said block copolymer is present in an amount of about 3.34 wt %.

43. The anti-corrosive agent of claim 40, wherein a weight ratio of the phosphoric acid to block copolymer to benzotriazole is about 2.24:1.49:1.

44. The anti-corrosive agent of claim 40, wherein the weight ratio of the phosphoric acid to block copolymer to benzotriazole is about 1.5:1:1 in an activated or use-dilution solution.

* * * * *